United States Patent
Greco et al.

(10) Patent No.: US 9,698,311 B2
(45) Date of Patent: Jul. 4, 2017

(54) BLUE LIGHT-EMITTING DIODES BASED ON ZINC SELENIDE QUANTUM DOTS

(71) Applicants: Fraunhofer-Gesellschaft zur Forderung der angewandten Forschung e.V., Munich (DE); Korea Electronics Technology Institute, Gyeonggi-do (KR)

(72) Inventors: Tonino Greco, Berlin (DE); Christian Ippen, Berlin (DE); Armin Wedel, Teltow (DE)

(73) Assignees: FRAUNHOFER-GESELLSCHAFT ZUR FORDERUNG DER ANGEWANDTEN FORSHUNG E.V. (DE); KOREA ELECTRONICS TECHNOLOGY INSTITUTE (KR)

( * ) Notice: Subject to any disclaimer, the term of this patent is extended or adjusted under 35 U.S.C. 154(b) by 0 days.

(21) Appl. No.: 14/244,539

(22) Filed: Apr. 3, 2014

(65) Prior Publication Data
US 2014/0353579 A1    Dec. 4, 2014

(30) Foreign Application Priority Data
Apr. 5, 2013  (DE) .................. 10 2013 206 077

(51) Int. Cl.
*H01L 33/26* (2010.01)
*H01L 33/44* (2010.01)
(Continued)

(52) U.S. Cl.
CPC .......... *H01L 33/44* (2013.01); *B01J 13/0004* (2013.01); *B01J 13/02* (2013.01); *B01J 13/22* (2013.01); *C09K 11/883* (2013.01); *G01N 33/588* (2013.01); *H01L 21/02474* (2013.01); *H01L 21/02477* (2013.01); *H01L 33/0087* (2013.01);
(Continued)

(58) Field of Classification Search
CPC . H01L 31/035218; H01L 33/28; B82Y 20/00; B82Y 40/00; Y10S 977/89; C09K 11/883
See application file for complete search history.

(56) References Cited

U.S. PATENT DOCUMENTS

2002/0144644 A1* 10/2002 Zehnder ................ B82Y 10/00
                                                                   117/84
2005/0051771 A1*  3/2005 Sato .................... B82Y 30/00
                                                                   257/40
(Continued)

FOREIGN PATENT DOCUMENTS

DE    11 2006 001 067    4/2005
EP        1 514 909 A2    3/2005
(Continued)

OTHER PUBLICATIONS

European Search Report dated May 15, 2014.
(Continued)

*Primary Examiner* — Eduardo A Rodela
*Assistant Examiner* — Christopher M Roland
(74) *Attorney, Agent, or Firm* — Tarolli, Sundheim, Covell & Tummino LLP (57) ABSTRACT

The present invention relates to colloidal quantum dots, to a process for producing such colloidal quantum dots, to the use thereof and to optoelectronic components comprising colloidal quantum dots.

12 Claims, 4 Drawing Sheets

(51) Int. Cl.

| | |
|---|---|
| *C09K 11/88* | (2006.01) |
| *H01L 21/02* | (2006.01) |
| *H01L 33/00* | (2010.01) |
| *H01L 33/28* | (2010.01) |
| *G01N 33/58* | (2006.01) |
| *B01J 13/00* | (2006.01) |
| *B01J 13/02* | (2006.01) |
| *B01J 13/22* | (2006.01) |
| *H01L 31/0352* | (2006.01) |
| *B82Y 20/00* | (2011.01) |
| *B82Y 40/00* | (2011.01) |

(52) U.S. Cl.
CPC .............. *H01L 33/28* (2013.01); *B82Y 20/00* (2013.01); *B82Y 40/00* (2013.01); *H01L 31/035218* (2013.01); *Y10S 977/89* (2013.01); *Y10S 977/95* (2013.01)

(56) References Cited

U.S. PATENT DOCUMENTS

| | | | |
|---|---|---|---|
| 2007/0034833 A1* | 2/2007 | Parce et al. | 252/301.36 |
| 2007/0057263 A1 | 3/2007 | Kahen | |
| 2007/0194694 A1* | 8/2007 | Reddy | 313/503 |
| 2011/0281740 A1* | 11/2011 | Beechem | C12Q 1/686 506/7 |
| 2013/0189803 A1* | 7/2013 | Nasaani et al. | 438/27 |
| 2014/0242631 A1* | 8/2014 | Yang et al. | 435/29 |

FOREIGN PATENT DOCUMENTS

| | | |
|---|---|---|
| EP | 1787659 A1 | 5/2007 |
| GB | 2470131 A | 11/2010 |
| WO | 2006116337 A1 | 11/2006 |
| WO | 2007057182 A2 | 5/2007 |
| WO | 2009025913 A2 | 2/2009 |

OTHER PUBLICATIONS

Cumberland, Scott L., et al., "Inorganic Clusters as Single-Source Precursors for Preparation of CdSe, ZnSe, and CdSe/Zns Nanomaterials", Chem. Mater. 2002, 14, 1576-1584.

Li, Lin Song, et al., "High Quality ZnSe and ZnS Nanocrystals Formed by Activating Zinc Carboxylate Precursors", Nano Letter 2004, vol. 4, No. 11, 2261-2264.

German Office Action dated Apr. 5, 2014.

Office Action for German Application No. 10 2013 206 007.7, dated Sep. 12, 2016.

* cited by examiner

BLUE LIGHT-EMITTING DIODES BASED ON ZINC SELENIDE QUANTUM DOTS

The present invention relates to the use of colloidal, solution-processible quantum dots as a light-emitting material in thin-film light-emitting diodes, especially to the use of zinc selenide quantum dots for generation of saturated blue light, and to processes for production and processing of these quantum dots.

Colloidal semiconductor nanoparticles, also called quantum dots, are of particular interest for use in optoelectronic components because of their optical properties. The advantageous properties of such colloidal quantum dots include good luminescence efficiencies, adjustability of the emission wavelength via the particle size, and especially the low width of the emission peak, which results in a high colour saturation. Furthermore, colloidal quantum dots are soluble in organic solvents, which enables the use of inexpensive and rapid solution-based processing methods, for example printing processes.

Particularly the use of the quantum dots as an emitter material in light-emitting diodes is of high interest for various reasons. The high luminescence efficiency of the quantum dots allows good light yields to be achieved and hence the energy consumption for displays and lighting to be lowered. By virtue of the narrow emission peaks, an exceptionally good colour saturation is achieved, as a result of which it is possible to extend the colour space of full-colour displays. The typically very rapid and simple production of quantum dots in a one-pot synthesis constitutes a cost advantage over other emitter materials such as organometallic complexes which are obtained in complex multistage synthesis processes with several associated purification steps. The solubility of the quantum dots in organic solvents allows inexpensive and flexible processing by means of printing processes.

Frequently, quantum dots are synthesized from II-VI semiconductors, primarily based on cadmium compounds such as CdSe, CdS or CdTe. Cadmium compounds, however, have a high toxicity. Furthermore, there exist relevant environmental regulations (for example the RoHS Directive in the European Union), which restrict or completely ban the use of cadmium-containing materials, as a result of which the prospects of real use of these quantum dots in optoelectronic components, for example, is low. There is therefore a need for quantum dots which are both cadmium-free and have an adequate luminescence quantum yield. Moreover, these quantum dots are to be producible in a simple manner.

As an alternative to the cadmium-containing materials mentioned for quantum dots, III-V semiconductors are frequently also proposed, for example indium phosphide or indium arsenide. Even though sweeping advances have been achieved in recent years in the development of these quantum dot materials, these materials are unsuitable for the emission of blue light, since the intrinsic bandgap of the corresponding bulk material is too small. Hypothetical blue-emitting quantum dots of these materials would therefore have to have a very small particle size, as a result of which they become thermodynamically unstable because of the high surface energy. Typically, it is possible with InP quantum dots to cover the range from blue-green to near infrared light; InAs quantum dots emit in the infrared region.

Further alternatives to cadmium-containing quantum dots are ternary or quaternary chalcopyrite compounds such as copper indium sulphide or copper indium gallium sulphide, but these cover only the range from yellow to near infrared light and additionally generally have a very broad emission peak because of stoichiometric inhomogeneity. Metal-doped zinc chalcogenides are further alternatives of interest, but the adjustability of the emission colour via the particle size is limited; instead, the doping material is crucial for the emission colour. Through manganese doping of zinc sulphide nanoparticles, yellow- or orange-emitting materials are obtainable; Cu doping also allows green-emitting materials.

There is therefore still a need for a cadmium-free quantum dot system which emits deep blue light with high efficiency and colour saturation, is easy to produce and can be processed by solution-based processes, and can be used, for example, in a thin-film light-emitting diode.

A problem addressed by present invention is accordingly that of providing cadmium-free quantum dots having the advantages of known cadmium-containing quantum dots. A particular problem addressed by the present invention is that of providing quantum dots which are both cadmium-free and have a good luminescence quantum yield. A further problem addressed is that of providing a synthesis for the said quantum dots which enables control of the particle size and the emission wavelength. An additional problem addressed is that of providing the quantum dots by a simple process. More particularly, the problem addressed is that of performing the process without purifying operations after the respective intermediate steps.

The solution to these and further problems is apparent from the subject-matter of the independent claims. Advantageous embodiments are apparent from the combination thereof with the features of the dependent claims.

In one aspect of the present invention, colloidal quantum dots are provided, comprising
 a) a core comprising zinc selenide (ZnSe)
 b) optionally one or more shells comprising zinc selenide grown onto the core
 c) at least one shell of a passivating material applied to the core and/or the last shell,
said colloidal quantum dots being cadmium-free.

In the context of the present invention, the term "colloidal" is understood in its customary meaning familiar to the person skilled in the art and relates to a dispersion of particles in another solid, liquid or gaseous medium.

In the context of the present invention, the term "quantum dot" is understood in its customary meaning familiar to the person skilled in the art and relates to a core of colloidal semiconductor nanoparticles on which several shells have been coated by epitaxial means.

In the context of the present invention, the term "core" relates to nanoparticles comprising semiconductor materials. The cores preferably consist of zinc selenide.

In the context of the present invention, the term "nanoparticles" is understood in its customary meaning familiar to the person skilled in the art and relates to particles which consist of an assembly of atoms or molecules and have a size between 1 and 100 nm.

In the context of the present invention, the term "shells" relates to layers comprising semiconductor materials or passivating materials surrounding the core. Preferably, the shells comprising semiconductor materials consist of zinc selenide and the shells comprising passivating materials of zinc sulphide.

In the context of the present invention, the term "epitaxial" relates to the application of the individual shells to the substrate, the first shell being grown onto the core and the further shells being grown onto the outer shell in each case.

In the context of the present invention, the term "passivation" relates to the production of a protective layer which protects the ZnSe particle surface from environmental influences and hence leads to an improved stability.

In the context of the present invention, the term "cadmium-free" in connection with the inventive colloidal quantum dots means that no cadmium compounds are used for synthesis of said quantum dots.

In a further aspect of the present invention, a process for producing colloidal quantum dots is provided, comprising:
 a) providing a raw solution comprising at least one zinc carboxylate,
 b) providing at least one selenium source,
 c) providing at least one sulphur source,
 d) contacting the raw solution comprising at least one zinc carboxylate from step a) with at least one selenium source from step b),
 e) optionally at least one further contacting operation for the reaction solution obtained from step d) with at least one further selenium source from step b), and
 f) contacting the solution obtained from step d) and/or step e) with at least one sulphur source from step c),
wherein the colloidal quantum dots are produced in a one-pot process and the particle size in steps d) and e) is defined via the stoichiometric ratio of the raw solution comprising at least one zinc carboxylate from step a) and the selenium source from step b) and/or via the number of growth steps in step e).

In the context of the present invention, the term "one-pot process" is understood in its customary meaning familiar to the person skilled in the art and relates to a synthesis process in which no purifying operations are conducted between the individual synthesis steps.

In a further aspect of the present invention, the inventive colloidal quantum dots are used in OLEDs, hybrid QD solar cells, as a stable fluorescent label in bioanalytics, in fluorescence collectors, as a luminescent safety feature, in X-ray scintillators, in organic field-effect transistors and in lighting technology.

In a further aspect of the present invention, a process for producing an optoelectronic component comprising at least one inventive colloidal quantum dot is provided.

In a further aspect of the present invention, a process for producing an optoelectronic component is provided, comprising:
 a) providing a transparent anode,
 b) providing a hole-injecting layer,
 c) providing a hole-conducting layer,
 d) providing a layer comprising quantum dots,
 e) providing an electron-conducting layer,
 f) optionally providing an electron-injecting layer, and
 g) providing a metal cathode,
wherein the optoelectronic component is produced in a layer structure and the quantum dot layer is applied to the hole-conducting layer by spin-coating, dip-coating, inkjet printing, gravure printing and/or spray-coating.

In an illustrative embodiment of the present invention, the emission wavelength of said colloidal quantum dots is between 400 and 460 nm, preferably between 400 and 450 nm, more preferably between 410 and 440 nm.

In an illustrative embodiment of the present invention, the particle size of said colloidal quantum dots is between 2 and 10 nm, preferably between 2.3 and 9 nm, further preferably between 5 and 8 nm.

In an illustrative embodiment of the present invention,
 a) the standard deviation for the size distribution of the colloidal quantum dots is not more than 20%, preferably not more than 15%, further preferably not more than 10% and/or
 b) the half-height width (FWHM) of the emission peak is 10 to 30 nm, preferably 15 to 20 nm.

The colloidal quantum dots according to the present invention comprise
 a) a core comprising zinc selenide
 b) at least one shell of a passivating material applied to the core,
said colloidal quantum dots being cadmium-free.

Optionally, one or more shells comprising zinc selenide may be grown onto the zinc selenide-comprising cores of the inventive colloidal quantum dots.

In a preferred embodiment of the present invention, the colloidal quantum dots consist of
 a) a core comprising zinc selenide
 b) one or more shells comprising zinc selenide grown onto the core
 c) at least one shell of a passivating material applied to the core and/or the last shell,
said colloidal quantum dots being cadmium-free.

As passivating material, it is possible with preference to use any compounds which protect the ZnSe particle surface from environmental influences.

Further preferably it is possible to use, as passivating material, compounds selected from the group encompassing ZnO, ZnS, MgO, MgS, MgSe, MgTe, CaO, CaS, CaSe, CaTe, AlN, GaN, GaP, GaAs, GaSb, SiC, TiN, BN, $SiO_2$, $TiO_2$, $ZrO_2$, $HfO_2$, $MoO_3$, $WO_3$, NiO, $Al_2O_3$, $In_2O_3$, and mixtures of these.

More preferably, the passivating material used is zinc sulphide (ZnS).

The ZnS shell passivates defects at the ZnSe particle surface, which leads to an improvement in the quantum yield and hence to higher device efficiencies. In addition, spectral impurities which are caused by defect states are eliminated by the passivation, which increases the colour saturation.

The inventive colloidal quantum dots do not contain any toxic heavy metals and are therefore not subject to any regulatory restrictions. Existing versions of blue-emitting quantum dot LEDs use carcinogenic cadmium-based quantum dots, which are of no relevance for use because of environmental legislation.

The emission wavelength of the inventive colloidal quantum dots can be adjusted via the size of the ZnSe core between 400 and 460 nm The emission wavelength of the inventive colloidal quantum dots is preferably between 400 and 460 nm, more preferably between 400 and 450 nm, further preferably between 410 and 440 nm.

The particle size is adjusted here via the stoichiometry of the precursors in the nucleation and growth phase and/or the number of ZnSe shells. Preferably, the particle size of the inventive colloidal quantum dots is between 2 and 10 nm, preferably between 2.3 and 9 nm, further preferably between 5 and 8 nm. The particle size is preferably determined by means of the electron microscopy method, which is familiar to those skilled in the art.

In the context of the present invention, the term "nucleation phase" relates to the formation of the ZnSe cores, and the term "growth phase" to the growth process of the ZnSe shells which have been applied to the core.

Preferably, the size of the ZnSe cores of the inventive colloidal quantum dots after the nucleation phase may be within a range from 1.5 to 2 nm After the optional application of one or more ZnSe shells, the particle size is preferably within a range from 2.4 to 6 nm.

For adjustment of the wavelength range, the layer thickness of the first and every further optional ZnSe shell is preferably within a range from 0.4 to 3.6 nm, further preferably within a range from 1.2 to 3 nm.

The layer thickness of the shell of a passivating material is preferably within a range from 0.3 to 3 nm, further preferably within a range from 2 to 3 nm.

The inventive colloidal quantum dots are obtained in excellent size distributions, as a result of which the peak of the bandgap emission is extremely narrow. Together with the controllability of the position of the emission peak, this allows perfect adjustability of the CIE colour coordinates of the blue light produced. Preferably, the standard deviation for the size distribution of the inventive colloidal quantum dots is not more than 20%, further preferably not more than 15%, especially preferably not more than 10%. Preferably, the half-height width (FWHM) of the emission peak of the inventive colloidal quantum dots is in the range from 10 to 30 nm, especially preferably in the range from 15 to 20 nm.

The inventive colloidal quantum dots are preferably coated with organic surface ligands.

The use of organic surface ligands allows dispersibility in nonpolar solvents, which enables the processing of the quantum dots by means of inexpensive and flexible solution processes such as spin-coating, dip-coating, inkjet printing, gravure printing and the like. At the same time, the organic content is optimized through the use of suitable ligands such that a high density of quantum dots is achieved in the thin layer and hence efficient functioning in the device is enabled.

Preferably, the inventive colloidal quantum dots can be coated using any organic surface ligands which enable dispersibility of the colloidal quantum dots in nonpolar solvents.

Further preferably, it is possible to use ligands selected from the group encompassing TOP (trioctylphosphine), TOPO (trioctylphosphine oxide), zinc carboxylate, carboxylic acids, amines, phosphonic acids and mixtures of these.

Preferably, the ZnSe cores of the inventive colloidal quantum dots have a ZnSe content in the range from 40 to 80% by weight, further preferably from 50 to 80% by weight.

The process for producing the colloidal quantum dots comprises, in one step, step a), the provision of a raw solution comprising at least one zinc carboxylate.

The raw solution comprising at least one zinc carboxylate is preferably obtained by the contacting of a zinc salt with at least one carboxylic acid.

Preferably, the zinc salts used may be any zinc salts having sufficient reactivity to obtain the corresponding zinc carboxylate.

Further preferably, zinc salts selected from the group encompassing zinc acetate, zinc fluoride, zinc chloride, zinc bromide, zinc iodide, zinc nitrate, zinc triflate, zinc tosylate, zinc mesylate, zinc oxide, zinc sulphate, zinc acetylacetonate, zinc toluene-3,4-dithiolate, zinc p-toluenesulphonate, zinc diethyldithiocarbamate, zinc dibenzyldithiocarbamate and mixtures of these are used.

Preferably, the carboxylic acids used may be any compounds having sufficient reactivity to obtain the corresponding zinc carboxylate.

Further preferably, carboxylic acids selected from the group encompassing acetic acid, propionic acid, butyric acid, valeric acid, caproic acid, heptanoic acid, caprylic acid, capric acid, undecanoic acid, lauric acid, myristic acid, palmitic acid, stearic acid, behenic acid, acrylic acid, methacrylic acid, but-2-enoic acid, but-3-enoic acid, pent-2-enoic acid, pent-4-enoic acid, hex-2-enoic acid, hex-3-enoic acid, hex-4-enoic acid, hex-5-enoic acid, hept-6-enoic acid, oct-2-enoic acid, dec-2-enoic acid, undec-10-enoic acid, dodec-5-enoic acid, oleic acid, gadoleic acid, erucic acid, linoleic acid, α-linolenic acid, calendic acid, eicosadienoic acid, eicosatrienoic acid, arachidonic acid, stearidonic acid, benzoic acid, para-toluic acid, ortho-toluic acid, meta-toluic acid, hydrocinnamic acid, naphthenic acid, cinnamic acid, para-toluenesulphonic acid and mixtures of these are used.

The zinc salts and carboxylic acids listed can be combined and used in any form. Particular preference is given to using zinc oxide as the zinc salt and caprylic acid as the carboxylic acid.

In order to convert the zinc salt to the corresponding zinc carboxylate, it is possible to use customary processes known to those skilled in the art.

The process for producing the colloidal quantum dots comprises, in one step, step b), the provision of at least one selenium source.

Preferably, the selenium sources used are compounds selected from the group encompassing trioctylphosphine selenide, tri(n-butyl)phosphine selenide, tri(sec-butyl)phosphine selenide, tri(tert-butyl)phosphine selenide, trimethylphosphine selenide, triphenylphosphine selenide, diphenylphosphine selenide, phenylphosphine selenide, cyclohexylphosphine selenide, octaselenol, dodecaselenol, selenophenol, elemental selenium dissolved in octadecene, selenium dioxide dissolved in octadecene, selenourea, bis(trimethylsilyl) selenide and mixtures of these.

Especially preferably, diphenylphosphine selenide is used as the selenium source.

The process for producing the colloidal quantum dots comprises, in one step, step c), the provision of at least one sulphur source.

Preferably, the sulphur sources used are compounds selected from the group encompassing elemental sulphur, octanethiol, dodecanethiol, octadecanethiol, tributylphosphine sulphide, cyclohexyl isothiocyanate, α-toluenethiol, ethylene trithiocarbonate, allyl mercaptan, bis(trimethylsilyl) sulphide, trioctylphosphine sulphide and mixtures of these.

Especially preferably, the sulphur source used is trioctylphosphine sulphide.

The process for producing the colloidal quantum dots comprises, in one step, step d), the contacting of the raw solution comprising at least one zinc carboxylate from step a) with at least one selenium source from step b).

Preferably, the zinc carboxylate is suspended in an organic solvent for the reaction. The solvents used may be any organic solvents. More particularly, the organic solvent may be selected from hydrocarbons having a boiling point of at least 250° C. and further preferably of at least 300° C. at standard pressure. For example, the organic solvent may be selected from octadecene and paraffin oil, preferably octadecene.

Preferably, in step d), the zinc carboxylate and the selenium source are present in a stoichiometric ratio in the range from 2:1 to 20:1; especially preferably, the stoichiometric ratio is 10:1.

In a preferred embodiment, the suspension of zinc carboxylate in an organic solvent is heated to an elevated reaction temperature in the range from 200 to 320° C., further preferably to 270 to 290° C. At this temperature, the selenium source is added, the zinc source preferably being in a significant excess of up to 20 stoichiometric equivalents, further preferably of up to 10 stoichiometric equivalents. The reaction mixture is left at the elevated reaction temperature selected for a certain period of up to 60 minutes, preferably less than 10 minutes.

The ZnSe core nanoparticles obtained have a very low emission wavelength in the range from about 380 to 410 nm. In order to shift this into the range up to 460 nm which is more relevant to the use, the process comprises an optional step, step e), which comprises at least one further contacting operation for the reaction solution obtained from step d) with at least one further selenium source from step b).

Preferably, the further selenium sources used are compounds selected from the group encompassing trioctylphosphine selenide, tri(n-butyl)phosphine selenide, tri(sec-butyl) phosphine selenide, tri(tert-butyl)phosphine selenide, trimethylphosphine selenide, triphenylphosphine selenide, diphenylphosphine selenide, phenylphosphine selenide, cyclohexylphosphine selenide, octaselenol, dodecaselenol, selenophenol, elemental selenium dissolved in octadecene, selenium oxide dissolved in octadecene, selenourea, bis (trimethylsilyl) selenide and mixtures of these.

The further selenium source need not be identical to the selenium source used in the first growth step. Preferably, the further selenium source is not identical to the selenium source used in the first growth step.

Especially preferably, the further selenium source used is trioctylphosphine selenide.

Preferably, the further selenium source is added at room temperature.

In a preferred embodiment, the reaction mixture, after addition of the further selenium source, is heated to a reaction temperature in the range from 200 to 320° C., more preferably from 270 to 290° C. The reaction mixture is left at the elevated reaction temperature selected for a certain period of up to 60 minutes, preferably 10 to 30 minutes.

The process for producing the colloidal quantum dots comprises, in one step, step f), the contacting of the reaction solution obtained from step d) and/or step e) with at least one sulphur source from step c).

In a preferred embodiment, the reaction mixture, after addition of the sulphur source, is heated to a reaction temperature in the range from 200 to 320° C., further preferably from 270 to 290° C. The reaction mixture is left at the elevated reaction temperature selected for a certain period of up to 60 minutes, preferably 10 to 30 minutes.

Step f) can be repeated in order to achieve a thicker passivation layer and hence better stability with respect to environmental influences.

After performance of these synthesis steps, the inventive colloidal quantum dots are separated from the solvent, from by-products and from unreacted precursors by repeated washing with a volatile polar solvent, for example butanone, acetone, isopropanol, ethanol, methanol, acetonitrile or mixtures thereof.

The process described offers the particular advantage that the inventive colloidal quantum dots can be produced in a one-pot process. This enables a process without purifying operations between the individual steps, which gives rise to a cost advantage over other processes.

Because of their advantageous properties, the inventive colloidal quantum dots can be used especially in OLEDs, hybrid QD-organic solar cells, as stable fluorescent labels in bioanalytics, in fluorescence collectors through embedding into transparent organic matrices, in security technology as a luminescent security feature, in novel X-ray beam scintillators, in organic field-effect transistors and in lighting technology.

Optoelectronic components in which the inventive colloidal quantum dots are used especially exhibit favourable narrow-band electroluminescence.

The process for producing an optoelectronic component comprises, in one step, step a), the provision of a transparent anode.

Preferably, said anode comprises indium tin oxide.

The process for producing an optoelectronic component comprises, in one step, step b), the provision of a hole-injecting layer.

Preferably, said hole-injecting layer comprises PEDOT: PSS (poly-3,4-ethylenedioxythiophene polystyrenesulphonate).

The process for producing an optoelectronic component comprises, in one step, step c), the provision of a hole-conducting layer.

Preferably, materials used as the hole-conducting layer are selected from the group encompassing poly-TPD (poly (N,N'-bis(4-butylphenyl)-N,N'-bis(phenyl)benzidine)), TAPC (1-bis[4-[N,N'-di(p-tolyl)amino]phenyl]cyclohexane), CBP (4,4'-bis(carbazol-9-yl)biphenyl), PVK (poly (N-vinylcarbazole)), TCTA (4,4',4"-tris(carbazol-9-yl)-triphenylamine), P3HT (poly(3-hexylthiophene-2,5-diyl)), MEH-PPV (poly[2-methoxy-5-(2-ethylhexyloxy)-1,4-phenylenevinylene]), $MoO_3$ (molybdenum trioxide), $ZrO_2$ (zirconium dioxide), NiO (nickel oxide), $WO_3$ (tungsten oxide) or mixtures thereof.

Especially preferably, the hole-conducting layer comprises TCTA.

The process for producing an optoelectronic component comprises, in one step, step d), the provision of a layer comprising the inventive colloidal quantum dots.

The process for producing an optoelectronic component comprises, in one step, step e), the provision of an electron-conducting layer.

Preferably, materials used as the electron-conducting layer are selected from the group encompassing TPBI (1,3,5-tris(1-phenyl-1H-benzimidazol-2-yl)benzene), ZnO (zinc oxide), $TiO_2$ (titanium dioxide), TBPO (2-(4-biphenyl)-5-(4-tert-butylphenyl)-1,3,4-oxadiazole) or mixtures thereof.

Especially preferably, the electron-conducting layer comprises TPBI.

The process for producing an optoelectronic component comprises, in an optional step, step f), the provision of an electron-injecting layer.

Preferably, materials used as the electron-injecting layer are selected from the group encompassing LiF, CsF, $Cs_2CO_3$ or mixtures thereof.

The process for producing an optoelectronic component comprises, in one step, step g), the provision of a metal cathode.

Preferably, metal cathodes comprising materials selected from the group encompassing Mg, Ba, Ca, Al, Ag, Au or mixtures thereof are used.

Especially preferably, metal cathodes comprising Ca/Ag are used.

The optoelectronic component is produced in a layer structure, each of the individual layers comprising the materials from steps a) to g).

The quantum dot layer is applied to the hole-conducting layer by spin-coating, dip-coating, inkjet printing, gravure printing and/or spray-coating.

Preferably, an organic solvent which does not damage the hole-conducting layer is used for the quantum dots.

Further preferably, the solvents used for the quantum dots are solvents selected from the group encompassing alkanes such as hexane, heptane, octane, nonane, decane, dodecane, undecane, cyclohexane, decalin or branched or cyclic isomers thereof, aromatics such as toluene, tetralin, benzene, chlorobenzene, o-dichlorobenzene, m-dichlorobenzene, p-dichlorobenzene, xylene, mesitylene, or mixtures thereof.

Especially preferably, the solvent used for the quantum dots is nonane.

WORKING EXAMPLES

Trioctylphosphine Selenide Stock Solution

Figure 1:
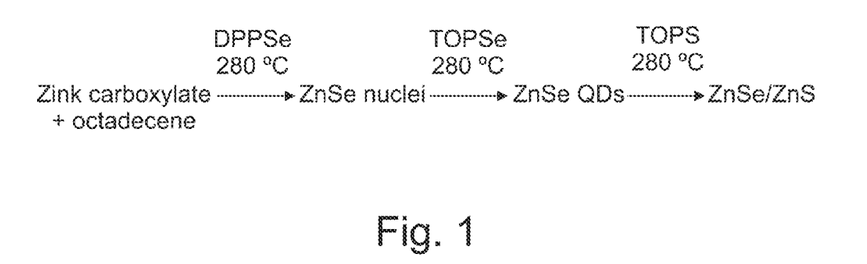
FIG. 1 shows the scheme for the one-pot synthesis of ZnSe/ZnS quantum dots with adjustable particle size. The synthesis comprises the ZnSe core nucleation, a ZnSe core growth step and a ZnS shell growth step.
Figure 2:
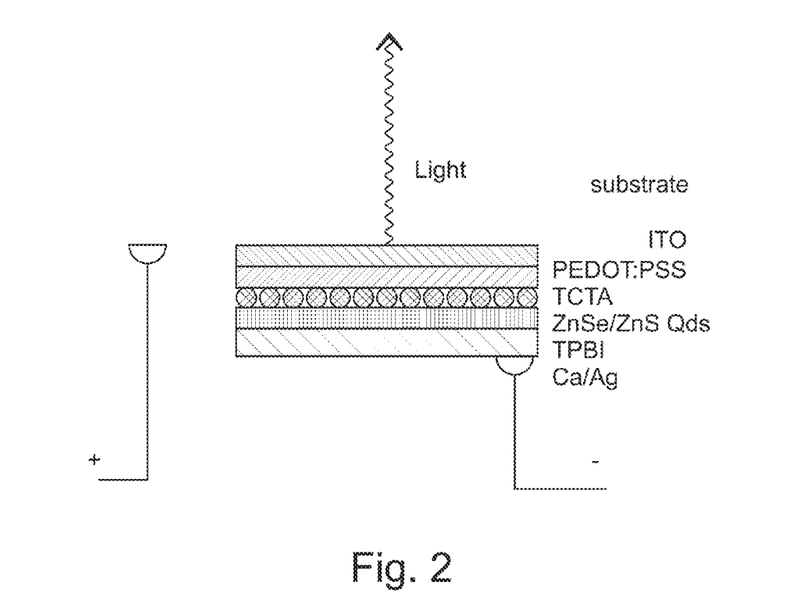
FIG. 2 shows the device scheme of a quantum dot LED with a monolayer of blue-emitting quantum dots and suitable charge carrier transport layers, and also electrodes.
Figure 3:
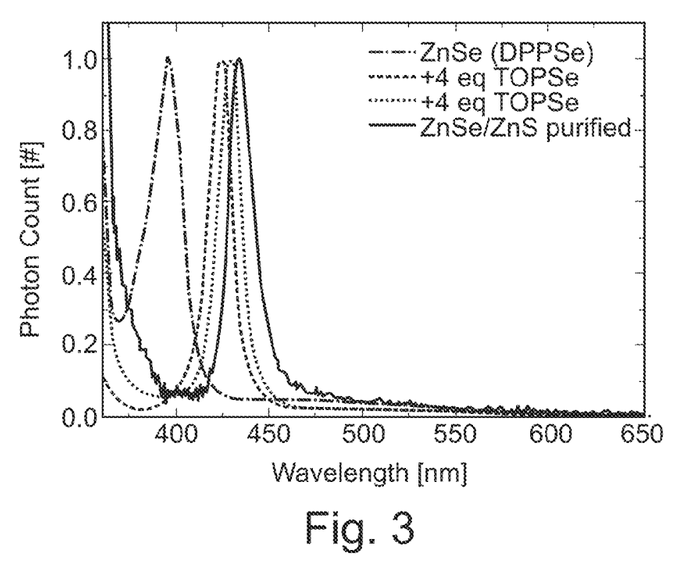
FIG. 3 shows the photoluminescence spectrum of the individual synthesis steps comprising core nucleation, core growth to shift the emission wavelength to 434 nm, and shell deposition, including workup and purification.
Figure 4:
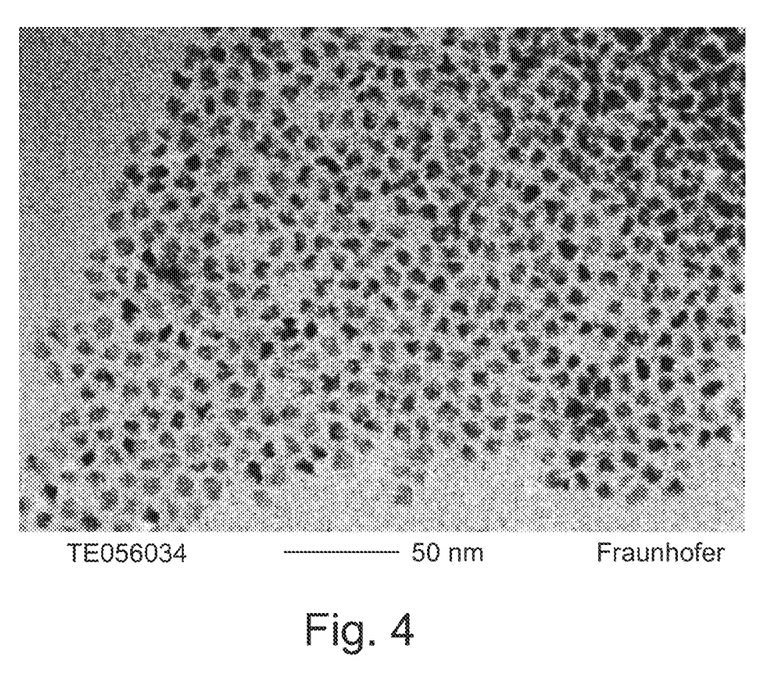
FIG. 4 shows a TEM image of ZnSe/ZnS quantum dots with an emission wavelength of 434 nm.
Figure 5:
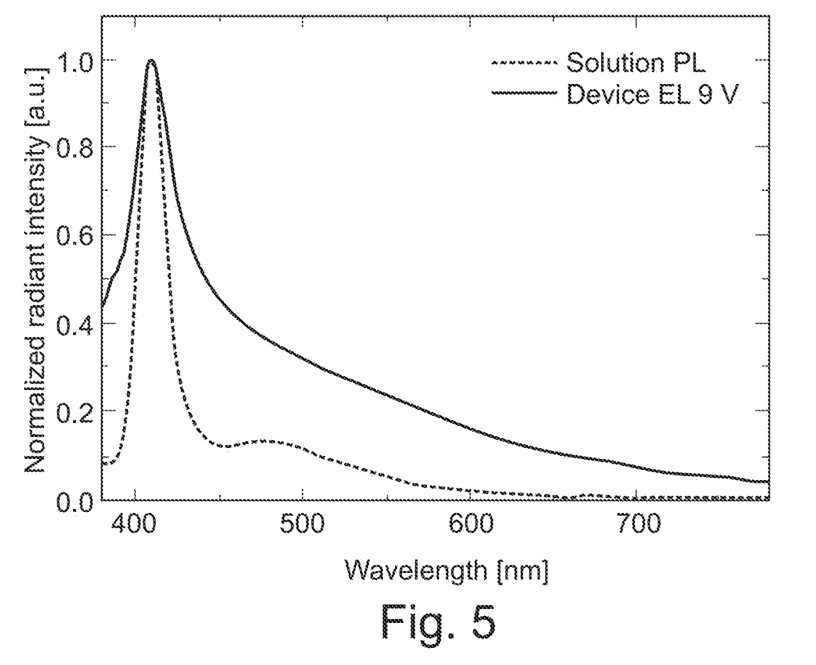
FIG. 5 shows photo- and electroluminescence spectra of ZnSe/ZnS quantum dots in nonane solution (PL) or as a thin layer in a device.
Figure 6:
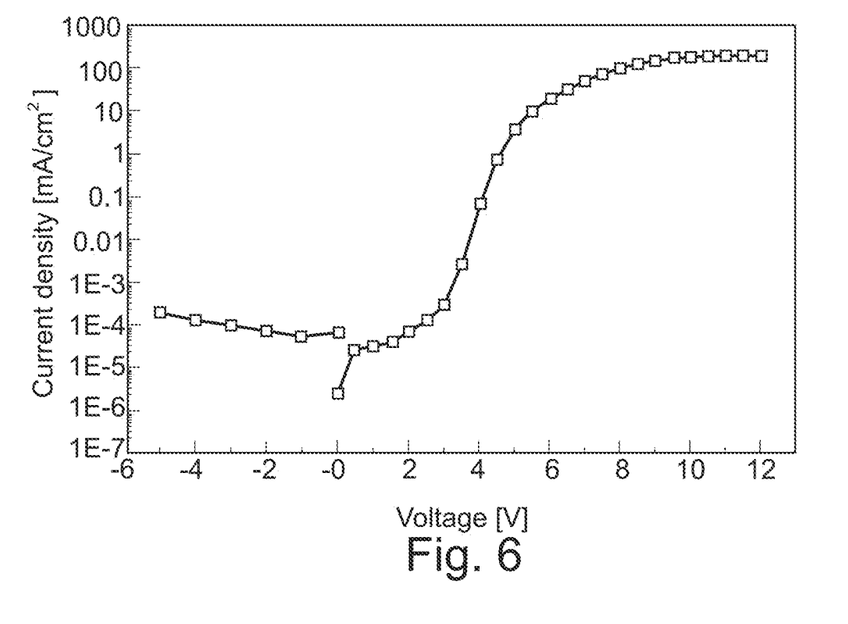
FIG. 6 shows the current density-voltage characteristic of a QLED comprising ZnSe/ZnS quantum dots.
Figure 7:
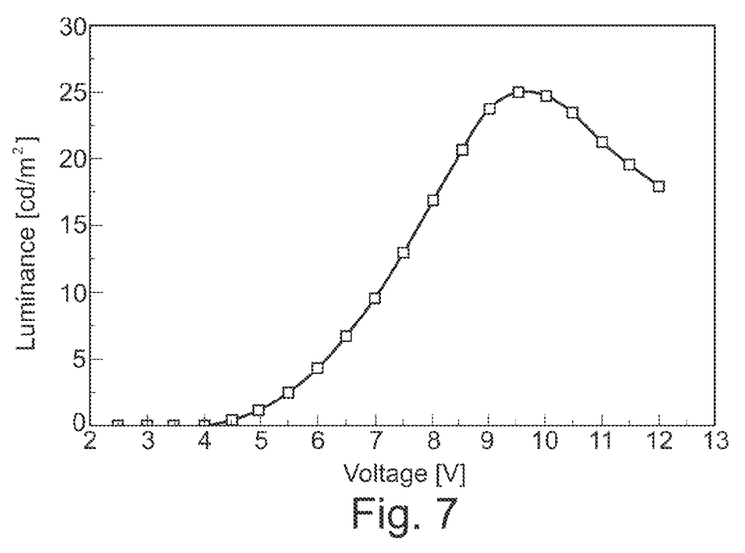
FIG. 7 shows the luminance-voltage characteristic of a QLED comprising ZnSe/ZnS quantum dots.
Figure 8:
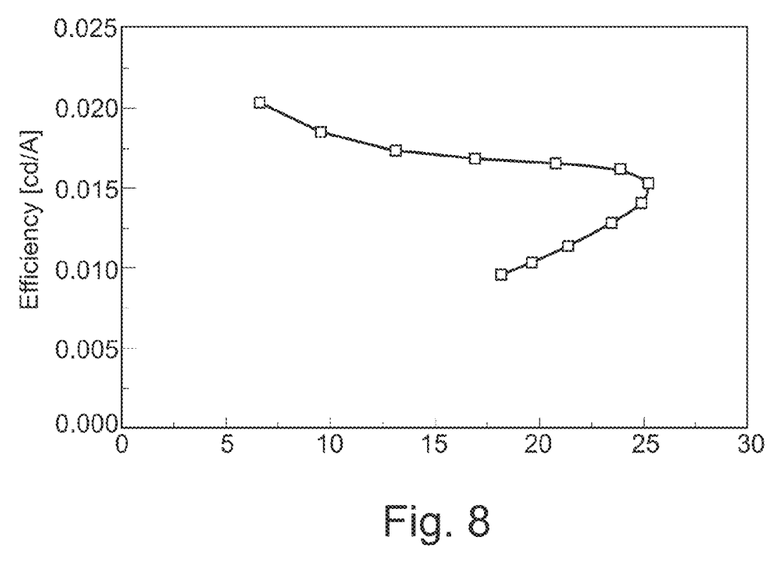
FIG. 8 shows the power efficiency-luminance characteristic of a QLED comprising ZnSe/ZnS quantum dots.

A stock solution of trioctylphosphine selenide in trioctylphosphine of concentration 1 M was prepared by the dissolution of elemental selenium (25 mmol, 2.0 g) in trioctylphosphine (25 ml). The mixture was stirred at 60° C. for several hours until a clear solution was obtained.

Diphenylphosphine Selenide Stock Solution

A stock solution of diphenylphosphine selenide in toluene of concentration 0.15 M was prepared by the dissolution of elemental selenium (53.7 mmol, 4.2 g) in diphenylphosphine (53.7 mmol, 10 g). The mixture was stirred at 120° C. under argon atmosphere for several hours until a clear orange melt was obtained. After cooling to room temperature, this was dissolved in 358 ml of anhydrous toluene.

Example

Zinc Caprylate Powder

Zinc caprylate was prepared by the reaction of zinc oxide (100 mmol, 8.1 g) with caprylic acid (200 mmol, 28.8 g) in a toluene suspension. The suspension was stirred under reflux conditions for a few hours until a clear solution was obtained. After removing the solvent, the zinc caprylate obtained was dried under reduced pressure at 50° C. for several hours.

Example

ZnSe Core Synthesis by Hot Injection

In a three-neck flask, zinc caprylate (1 mmol, 0.35 g) was suspended in 1-octadecene (2 ml) and placed under an inert atmosphere by repeated evacuation and flooding with argon. The mixture was heated to 280° C. while stirring, giving a clear solution. At this temperature, diphenylphosphine selenide (0.1 mmol, 0.67 ml of a 0.15 M stock solution in toluene) was added by rapid injection. The toluene was removed by means of an argon stream. The reaction mixture was kept at 280° C. for five minutes and then cooled to room temperature. The pale yellow solution obtained luminesces at 395 nm, FHWM 23 nm, QY 24%.

ZnSe Growth

To a raw solution of ZnSe core particles was added, at room temperature, trioctylphosphine selenide (0.4 mmol, 0.4 ml of a 1 M stock solution in trioctylphosphine). The mixture was heated to 280° C., kept at that temperature for 20 minutes, and then cooled to room temperature. The particle solution obtained luminesces at 423 nm, FWHM 15 nm, QY 33%.

ZnS Shell Synthesis

To a raw solution of ZnSe nanoparticles were added, in an argon countercurrent, zinc caprylate (1 mmol, 0.35 g) and trioctylphosphine sulphide (1 mmol, 1 ml of a stock solution in trioctylphosphine). The mixture was heated to 280° C., kept at that temperature for 20 minutes, and then cooled to room temperature. The core-shell particles obtained were precipitated with acetone and washed repeatedly, in order to obtain 80 g of the yellow nanoparticle powder. According to thermogravimetry analysis, the proportion of the organic components is 76 wt.-%. After redispersion in nonane, the particles luminesce at a wavelength of 434 nm, FWHM 16 nm, QY 8%.

Device Preparation

Glass substrates coated with ITO (indium tin oxide) were cleaned by rinsing with acetone, isopropanol and water and dried in a nitrogen stream. PEDOT:PSS (poly-3,4-ethylenedioxythiophene polystyrenesulphonate, Heraeus) was applied to the ITO substrates by spin-coating from a methanol/isopropanol/water mixture and the layer was subsequently heat-treated at 180° C. for 60 min Subsequently, TCTA (4,4',4"-tris(carbazol-9-yl)triphenylamine, Sensient) was spun onto the PEDOT layer from a toluene solution. The TCTA layer was dried at 130° C. for 30 min. The ZnSe/ZnS core-shell quantum dots were dispersed in nonane and likewise applied to the TCTA layer by spin-coating, and then the ZnSe layer was dried at 100° C. for 30 min.

Subsequently, thin layers of TPBI (1,3,5 -tris(1-phenyl-1H-benzimidazol-2-yl)benzene, LumTec), calcium and silver were applied successively by thermal vaporization. After the samples had been encapsulated, they were characterized by electrooptical means. All process steps were executed in a glovebox system under inert atmosphere.

The invention claimed is:

1. Colloidal quantum dots comprising:
    a) a core comprising zinc selenide;
    b) one or more shells comprising zinc selenide grown onto the core, thereby obtaining a last shell; and
    c) at least one shell of a ZnS passivating material applied to at least one of the core or the last shell,
    said colloidal quantum dots being cadmium-free; and
    wherein a standard deviation for a size distribution of the colloidal quantum dots is not more than 10%.

2. Colloidal quantum dots according to claim 1 having an emission wavelength between 400 and 460 nm.

3. Colloidal quantum dots according to claim 1 having a half-height width (FWHM) of emission peak within a range from 10 to 30nm.

4. Colloidal quantum dots according to claim 1, being provided in OLEDs, hybrid QD solar cells, as a stable fluorescent label in bioanalytics, in fluorescence collectors, as a luminescent security feature, in X-ray scintillators, in organic field-effect transistors and in lighting technology.

5. Colloidal quantum dots according to claim 1, being provided in an optoelectronic component comprising a transparent anode, a hole-injecting layer, a hole-conducting layer, an electron-conducting layer, optionally an electron-injecting layer and a metal cathode.

6. Colloidal quantum dots according to claim 1, wherein said quantum dots have a particle size between 2 and 10 nm.

7. Process for producing colloidal quantum dots according to claim 1, comprising:
   a) providing a raw solution comprising at least one zinc carboxylate,
   b) providing at least one selenium source,
   c) providing at least one sulfur source,
   d) contacting the raw solution comprising at least one zinc carboxylate from step a) with at least one selenium source from step b), thereby obtaining a reaction solution comprising particles having a particle size,
   e) the reaction solution obtained from step d) with at least one further selenium source from step b) in at least one growing step thereby obtaining another reaction solution comprising particles having a particle size, and
   f) contacting the reaction solution obtained from at least one of step d) or step e) with at least one sulfur source from step c),
   wherein the colloidal quantum dots are produced in a one-pot process and the particle size in steps d) and e) is defined via the stoichiometric ratio of the raw solution comprising at least one zinc carboxylate from step a) and the selenium source from step b) or via the number of growth steps in step e).

8. Process according to claim 7, wherein the raw solution comprising at least one zinc carboxylate is obtained by contacting a zinc salt selected from the group consisting of zinc acetate, zinc fluoride, zinc chloride, zinc bromide, zinc iodide, zinc nitrate, zinc triflate, zinc tosylate, zinc mesylate, zinc oxide, zinc sulphate, zinc acetylacetonate, zinc toluene-3,4-dithiolate, zinc p-toluene-sulphonate, zinc diethyldithiocarbamate, zinc dibenzyldithiocarbamate and mixtures of these, with at least one carboxylic acid selected from the group consisting of acetic acid, propionic acid, butyric acid, valeric acid, caproic acid, heptanoic acid, caprylic acid, capric acid, undecanoic acid, lauric acid, myristic acid, palmitic acid, stearic acid, behenic acid, acrylic acid, methacrylic acid, but-2-enoic acid, but-3-enoic acid, pent-2-enoic acid, pent-4-enoic acid, hex-2-enoic acid, hex-3-enoic acid, hex-4-enoic acid, hex-5-enoic acid, hept-6-enoic acid, oct-2-enoic acid, dec-2-enoic acid, undec-10-enoic acid, dodec-5-enoic acid, oleic acid, gadoleic acid, erucic acid, linoleic acid, α-linolenic acid, calendic acid, eicosadienoic acid, eicosatrienoic acid, arachidonic acid, stearidonic acid, benzoic acid, para-toluic acid, ortho-toluic acid, meta-toluic acid, hydrocinnamic acid, naphthenic acid, cinnamic acid, para-toluenesulphonic acid and mixtures of these.

9. Process according to claim 7, wherein the selenium source is selected from the group consisting of trioctylphosphine selenide, tri(n-butyl)phosphine selenide, tri(sec-butyl) phosphine selenide, tri(tert-butyl) phosphine selenide, trimethylphosphine selenide, triphenylphosphine selenide, diphenylphosphine selenide, phenylphosphine selenide, cyclohexylphosphine selenide, octaselenol, dodecaselenol, selenophenol, elemental selenium dissolved in octadecene, selenium dioxide dissolved in octadecene, selenourea, bis (trimethylsilyl) selenide and mixtures of these.

10. Process according to claim 7, wherein the sulfur source is selected from the group consisting of elemental sulfur, octanethiol, dodecanethiol, octadecanethiol, tributylphosphine sulphide, cyclohexyl isothiocyanate, α-toluenethiol, ethylene trithiocarbonate, allyl mercaptan, bis(trimethylsilyl) sulphide, trioctylphosphine sulphide and mixtures of these.

11. Process according to claim 7, wherein
   (i) the raw solution comprising at least one zinc carboxylate from step a), before being contacted with the selenium source from step b) in step d), is heated to a temperature within a range from 200° C. to 320° C.,
   (ii) the reaction solution of a further selenium source from step b), obtained from step d), is contacted and, after contacting, is heated to a temperature within a range from 200° C. to 320° C., and
   (iii) the reaction solution obtained from at least one of step d) or step e), after being contacted with the sulfur source from step c), is heated to a temperature within a range from 200° C. to 320° C.

12. Process for producing an optoelectronic component comprising:
   a) providing a transparent anode,
   b) providing a hole-injecting layer,
   c) providing a hole-conducting layer,
   d) providing a layer comprising quantum dots according to claim 1,
   e) providing an electron-conducting layer,
   f) optionally providing an electron-injecting layer, and
   g) providing a metal cathode,
   wherein the optoelectronic component is produced in a layer structure and the quantum dot layer is applied to the hole-conducting layer by spin-coating, dip-coating, inkjet printing, gravure printing and/or spray-coating.

* * * * *